United States Patent [19]

Jansma et al.

[11] Patent Number: 4,508,594
[45] Date of Patent: Apr. 2, 1985

[54] POLYALDEHYDE/POLYACETAL COMPOSITIONS

[75] Inventors: Roger H. Jansma, Park Forest; Karen R. Sandberg, West Chicago, both of Ill.

[73] Assignee: Nalco Chemical Company, Oak Brook, Ill.

[21] Appl. No.: 625,421

[22] Filed: Jun. 28, 1984

[51] Int. Cl.³ .............................................. D21H 3/38
[52] U.S. Cl. .................... 162/135; 162/164.1; 162/164.6; 162/164.7; 162/168.1; 162/168.2; 162/168.3; 162/168.7; 427/391; 427/395
[58] Field of Search ............... 162/164.1, 168.1, 168.2, 162/168.3, 168.6, 166, 135, 164.3; 427/391, 395; 8/116.4, 181, 194, 116 R; 526/320

[56] References Cited

U.S. PATENT DOCUMENTS

| | | | |
|---|---|---|---|
| Re. 28,474 | 7/1974 | Anderson et al. | 260/29.6 |
| Re. 28,576 | 10/1975 | Anderson et al. | 260/29.6 |
| 2,345,543 | 3/1944 | Wohnsiedler et al. | 260/72 |
| 2,582,840 | 1/1952 | Maxwell | 162/166 |
| 2,596,014 | 5/1952 | Dudley et al. | 162/166 |
| 3,080,281 | 3/1963 | Fischer et al. | 162/164.1 |
| 3,197,447 | 7/1965 | Talet | 526/320 |
| 3,210,327 | 10/1965 | Galiano et al. | 526/320 |
| 3,284,393 | 11/1966 | Vanderhoff et al. | 260/29.6 |
| 3,316,216 | 8/1967 | Fawcett et al. | 162/164.3 |
| 3,530,167 | 9/1970 | Dowbenko | 526/320 |
| 3,556,932 | 1/1971 | Coscia et al. | 162/164.1 |
| 3,625,926 | 12/1971 | Dowbenko | 526/320 |
| 4,448,908 | 5/1984 | Pauly et al. | 523/201 |

OTHER PUBLICATIONS

Polymer, Sep. 1974, vol. 15, authored by R. Epton, et al., Titled: Crosslinked poly(acryloylaminoacetaldehyde dimethylacetal) and derived urease conjugates.
Tetranedron, vol. 29, pp. 2147 to 2151, 1973, Article: N-alkylation of Nitriles–I.
Journal Am. Chem. Soc., vol. 57, p. 57ff, 1935, Titled: Improved Hydroxylamine Method for the Determination of Aldehydes and Ketones, Bryant, et al.
Scandanavian Pulp, Paper & Board Testing Committee Scan-C 35:81, and Scan-M 12:81, Titled: Initial Wet Web Tensin Strength, Stretch & Tensil Energy Absorption.
Tappi, 65 (3) 135, 1935, R. S. Seth, et al., Titled: The Strength of wet webs: a new approach.

*Primary Examiner*—Peter Chin
*Attorney, Agent, or Firm*—John G. Premo; Robert A. Miller; Donald G. Epple

[57] ABSTRACT

Water-soluble monomers and water-soluble polymers derived therefrom are disclosed. These materials can be used with other vinyl monomers to form water-soluble polymers which are reactive with cellulosic substrates to obtain drastically improved strength, particularly when applied in paper manufacture.

The polymers contain at least two mole percent of a monomer represented by the chemical structure:

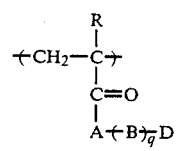

wherein
R is —H, —CH₃, or —C₂H₅; and
A is O, or N(R₁); and
B is CH₂, CH₂CH₂O, —(CH₂)ₙ N(R₁) (CH₂)ₘ,

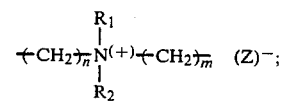

and
D is

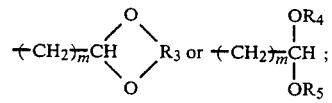

and
wherein R₁ is —H, —CH₃, —C₂H₅, (CH₂CH₂O)ₙ H, or (B)_q D, and wherein q is from 1–6, except when B contains nitrogen in which case q is always one; and wherein R₂ is —H, —CH₃, —C₂H₅, or (CH₂CH₂O)ₙH; and wherein R₃ is

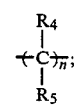

and
wherein R₄ and R₅ may be the same or different and are, for each individual occurance, —H, —CH₃, or —C₂H₅; and wherein Z is from the group Cl, Br, I, NO₃, SO₄ and the like; and wherein m ranges from 0–6; and wherein n is from 1–6.

3 Claims, No Drawings

POLYALDEHYDE/POLYACETAL COMPOSITIONS

INTRODUCTION

The present invention relates to new hydrophilic, water-soluble or dispersible vinyl polymers which, when dissolved in water and reacted with cellulosic fibrous materials, combine with these cellulosic materials to form a paper composition having greatly improved strength properties.

Three types of paper strength are significantly improved:

1. Wet Web Strength, which is the strength of never-been-dried paper in the range of about 20–60% solids content (balance is water). This property is particularly important as it relates to the reliable running of a paper machine.

2. Wet Strength (or "Rewetted Strength"), which is the strength of paper which has been fully dried which is then rewetted by water and the strength determined. This is differentiated from wet web strength in that opportunity for curing reactions has occured in the hot dryer section of a paper machine. This curing is frequently necessary for wet strength resins to achieve their performance.

3. Dry Strength, which is the strength of the final dry paper.

The water-soluble polymers of this invention have the property of imparting improved strength to paper sheet by a combination of these polymers with cellulosic fibers making up the paper sheet to form a new composition of matter which is a paper sheet composition having improved dry strength and improved wet strength and improved wet web strength and comprising cellulosic fibers combined with a water-soluble polymer which contains at least 2 mole percent of a monomer represented by the chemical structure:

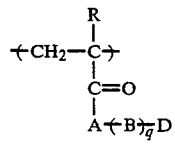

wherein
R is —H, —CH$_3$, or —C$_2$H$_5$; and
A is O, or N(R$_1$); and
B is CH$_2$, CH$_2$CH$_2$O, $-$(CH$_2$)$_n$N(R$_1$)(CH$_2$)$_m$,

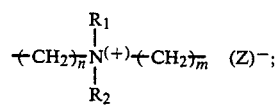

and
D is

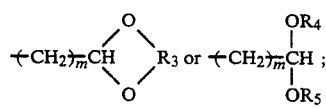

and
wherein R$_1$ is —H, —CH$_3$, —C$_2$H$_5$, (CH$_2$CH$_2$O)$_n$H, or (B)$_q$D, and wherein q is from 1–6, except when B contains nitrogen in which case q is always one; and wherein R$_2$ is —H, —CH$_3$, —C$_2$H$_5$, or (CH$_2$CH$_2$O)$_n$H; and wherein R$_3$ is

and
wherein R$_4$ and R$_5$ may be the same or different and are, for each individual occurance, —H, —CH$_3$, or —C$_2$H$_5$; and wherein Z is from the group Cl, Br, I, NO$_3$, SO$_4$ and the like; and wherein m ranges from 0–6; and wherein n is from 1–6.

Where we use R$_3$ as

we mean to include cyclic acetals such as:

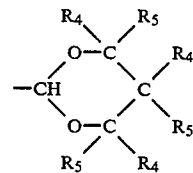

Wherein each individual occurence of R$_4$ and R$_5$ may be from the group —H, —CH$_3$, and —C$_2$H$_5$. In this way, cyclic structures such as:

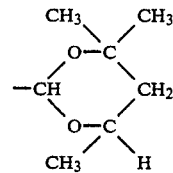

are included in our invention.

It is, therefore, an object of this invention that new vinyl monomers be synthesized having free aldehyde, acetal, or hemiacetal structures which, when reacted with similar monomers or copolymerized with other monomers, form water-soluble polymers which, when combined with cellulosic fibers, form an improved paper sheet having improved wet strength properties.

It is another object of this invention to provide for the synthesis of new compositions of water-soluble polymers containing reactive aldehyde, acetal, or hemiacetal functionality having the capability to react with cellulosic substrates to improve wet web strength, wet strength, dry strength, and other properties.

It is another object of this invention to provide methods and techniques for forming the polymers of this invention which, when combined with cellulosic fibers, achieve the improved strength properties cited above.

It is also an object of this invention to provide the types of polymers which can form improved paper sheet having strength properties heretofore not found in the art.

Finally, it is an object of this invention to form an improved paper sheet having strength properties exceeding any strength found in the art. And, it is an object of this invention to allow the manufacturer of paper sheet products to achieve higher manufacturing rates, lower costs per manufactured ton of paper, and higher quality paper products with less discard due to paper tearing in the manufacturing process because of the new paper compositions of this invention.

PRIOR ART

Ionic water-soluble polymers often have the property of imparting wet strength to paper and are especially important in the papermaking art because wet strength property allows for improved paper sheet making, faster manufacturing rates, and higher quality paper sheet products. U.S. Pat. Nos. 2,345,543, 2,582,840, 2,596,014, and 3,556,932 are just a few of the patents covering the attempts various parties have made to solve the problem presented by paper which is not treated to improve its wet strength properties. U.S. Pat. No. 3,556,932 particularly points out an improvement which is the discovery that ionic water-soluble vinyl amide polymers which have been made thermosetting by reason of reacted glyoxal possess beneficial properties to form wet strength agents in the manufacture of paper sheet. It is claimed in this patent that the ionic water-soluble vinyl amide polymers reacted with glyoxal are thermosetting and cure rapidly at neutral pH's to impart excellent wet strength to the paper sheet formed in the presence of this reacted polymer. The polymers are also taught to impart improved dry strength in addition to the more important wet strength properties. The polymers of this U.S. Pat. No. 3,556,932, which is incorporated herein by reference, can be prepared in either cationic or anionic form where the cationic polymers are self-substantive to the cellulosic fiber when contacted with said fibers in aqueous suspension. It is taught that the anionic polymers can be deposited on the cellulosic fibers with the aid of alum, a technique known in the art.

However, the polymers of this reference are the combination of water-soluble polyvinyl amides with glyoxal which formed a substituted, possibly crosslinked system, which is found to be thermosetted and provides the improved wet strength. This admixture is subject to chemical equilibrium which can cause difficulties in product stability if the admixture is not used appropriately.

U.S. Pat. No. 4,448,908, Pauly et. al., teaches a latex reactive with a biologically active substance forming a conjugate suitable for serological or immunological assay procedures where the latex contains a polymer core and a shell thereover, the shell comprises a water-insoluble monomer of the formula:

$$CH=C-C(=O)-N(H)-(CH_2)_n-CH(OR_3)(OR_4)$$
with substituents $R_1$, $R_2$

These monomers are used in this invention to achieve stability of immunologically active materials. This use is considerably different from the use anticipated in the instant invention.

The polymers of the instant invention do not have this drawback and can be stored for long periods in a form which is less reactive and then subsequently used as desired to obtain the improved strength for paper sheet. The polymers of this invention may be ionic in nature or they may be neutral and still perform their function. However, because cationic polymers are self-substantive to the cellulosic fiber, it is preferred that the water-soluble polymer used in this invention be a polymer which has incorporated therein some degree of cationic character. An advantage to using some of the monomers of this invention to form the water-soluble polymers of this invention which are used to manufacture the improved strength paper sheet of this invention is that the monomers and, hence, the polymers formed therefrom will contain aldehyde, acetal, or hemiacetal substantive functionality and may also contain cationic or anionic functionality.

In addition, a reference appearing in the journal, *Polymer*, September, 1974, Vol. 15, authored by R. Epton, et al., teaches the formation of water-insoluble crosslinked poly(acrylolylaminoacetaldehyde dimethyl acetal) and derived urease conjugates. These water-insoluble polymers are hydrolyzed leading to polyaldehydrol gels which were subsequently used to immobilize urease enzymes. These immobilized urease enzyme materials demonstrated greater stability during continuous use in columns, in storage and aqueous buffer suspensions, and to removal of substrate and to temperature changes. The synthesis of these water-insoluble gels, the mode of binding enzymes, and the mechanism of substrate inhibition for the polyaldehydrol-urease conjugates are discussed in this paper.

The polymers of the instant invention are water-soluble and are used after hydrolysis to form reactive materials which can be combined with cellulosic fibers to improve strength on a paper sheet. The teachings of Epton, et al., which are incorporated by reference herein, do not anticipate the teachings of this invention.

THE INVENTION

Our invention is a vinyl monomer capable of being polymerized by free radical or other initiators and represented by the chemical structure: (After vinyl polymerization)

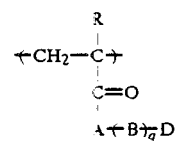

wherein
R is —H, —CH$_3$, or —C$_2$H$_5$; and
A is O, or N(R$_1$); and
B is CH$_2$, CH$_2$CH$_2$O, $+$CH$_2+_{\overline{n}}$N(R$_1$) (CH$_2+_{\overline{m}}$,

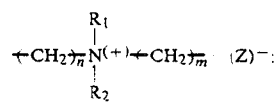

and
D is

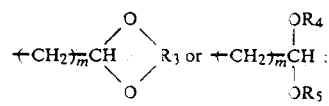

and wherein $R_1$ is —H, —$CH_3$, —$C_2H_5$, $(CH_2CH_2O)_nH$, or $(B)_nD$, and wherein q is from 1–6, except when B contains nitrogen in which case q is always one; and wherein $R_2$ is —H, —$CH_3$, —$C_2H_5$, or $(CH_2CH_2O)_nH$; and wherein $R_3$ is

and
wherein $R_4$ and $R_5$ may be the same or different and are for each individual occurrence, —H, —$CH_3$, or —$C_2H_5$; and wherein Z is from the group Cl, Br, I, $NO_3$, $SO_4$ and the like; and wherein m ranges from 0–6; and wherein n is from 1–6.

As can be seen above, the monomers of this invention are either substituted esters or substituted amides of acrylic, methacrylic or ethacrylic acid or acrylamide, methacrylamide, or ethacrylamide. The monomers contain an aldehyde, acetal, or hemiacetal, depending upon the state in which the monomer is found or the chemical environment in which the monomer is found. In addition, these monomers may contain oleophilic character of varying degree, or cationic character of varying degree. When the nitrogen compound which may be found in the —$(B)_qD$— substitution is quaternized, the material is strongly cationic and carries with it a gegenion which is chosen from the group consisting of chloride, bromide, iodide, methyl sulfate and the like. This gegenion may be changed by ion exchange techniques known in the art to provide salts such as nitrate, sulfate, phosphate, and the like.

There are several synthetic techniques that are available to form the vinyl monomers of this invention. One technique is to react a vinyl monomer acid halide with a substituted amino or alcohol compound which contains an acetal group in the following reactions:

1. 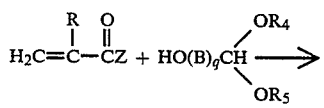

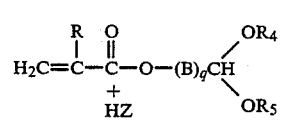

2. 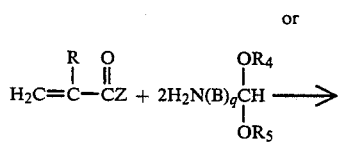

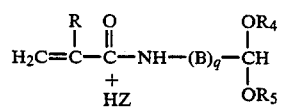

where Z=Cl, Br, I, and B, q, R, $R_4$ and $R_5$ have their previous meaning.

Other chemical reactions may also be used to synthesize the monomers of the instant invention. For example, an article appearing in *Tetrahedron*, Vol. 29, pages 2947–51 (1973), which is incorporated herein by reference, teaches the N-alkylation of nitriles as a general synthesis of substituted amidines. This reference applies nitrilium salt chemistry to the preparation of amidines which, by analogue, may be applied to the preparation of substituted acrylamide monomer using the following reaction sequence:

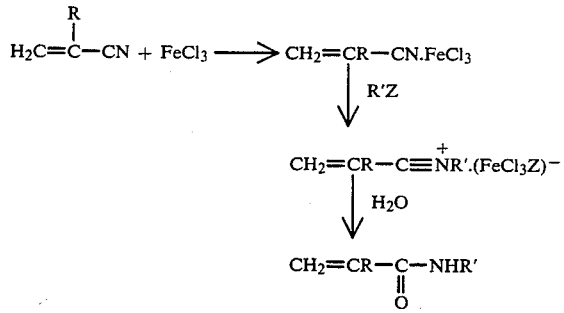

where R' may be

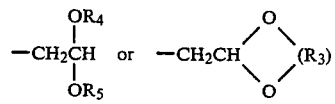

and the like, and where $R_3$, $R_4$ and $R_5$ have the same meaning as above and where Z=Cl, Br, I, and n is 1–6.

If other substantive functionality is desired in the monomers, they may be obtained by providing them originally in the acetal form above or in the R' group in the second sequence of reactions.

However, another sequence of reactions may be available to form compounds which are reactive, when synthesized as polymeric materials, with cellulosic fibers to improve paper strength. For example, the reaction sequence:

REACTANTS

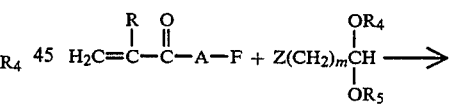

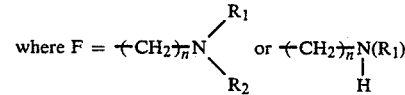

PRODUCTS

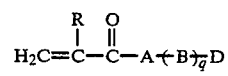

B is 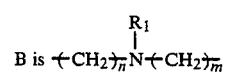

or

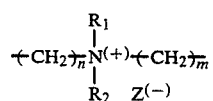

-continued $$\text{and D is: } -(CH_2)_m-\overset{OR_4}{\underset{OR_5}{CH}}$$

and where all other symbols have their above stated meanings, should yield reactive monomers which have cationic charge internally as well as the aldehyde, acetal, or hemiacetal structures.

The monomers found to be most useful are those in which

R is H or —$CH_3$,
A is $$-O-\quad \text{or} \quad -\overset{R_1}{\underset{}{N}}-,$$

B is —$CH_2$—, $$\displaystyle +CH_2\displaystyle\!\!+_{\overline{n}}\overset{R_1}{\underset{}{N}}+CH_2\displaystyle\!\!+_{\overline{m}} \text{ or } +CH_2\displaystyle\!\!+_{\overline{n}}\overset{R_1}{\underset{R_2}{N^+}}+CH_2\displaystyle\!\!+_{\overline{m}}, \text{ and}\quad Z^-$$

$$\text{D is } +CH_2)_m\overset{OR_4}{\underset{OR_5}{CH}} \quad +CH_2)_m-CH\overset{O}{\underset{O}{\diagdown}}R_3,$$

wherein the designations for $R_1$, $R_2$, $R_3$, m, n, Z, $R_4$, and $R_5$ are the same as above.

The most preferred vinyl monomers used to synthesize the water-soluble polymers of this invention are represented by the structures above where:

R is H or —$CH_3$,
A is —O— or —NH—
B is —$CH_2$—, and
D is $$(CH_2)_m-CH\overset{OR_4}{\underset{OR_5}{\diagdown}} \quad \text{or} \quad (CH_2)_mCH\overset{O}{\underset{O}{\diagdown}}R_3,$$

wherein $R_4$ and $R_5$ may be the same or different and may be each individually chosen from the group consisting of H, —$CH_3$, or —$C_2H_5$; and $R_3$ is $$+C\!\!+_{\overline{n}}\!\overset{R_4}{\underset{R_5}{\diagdown}},$$

m is 0–2, and where n is from 1–3.

THE WATER-SOLUBLE POLYMERS

To obtain the improved strength on paper of this invention, the monomers described above must be polymerized to obtain a water-soluble polymer which contains at least 2 mole percent of the monomers represented above. Preferably, the water-soluble polymers contain at least 10 mole percent of the above represented monomers and, most preferably, the water-soluble polymers contain at least 50 mole percent of the monomers represented by the chemical structures above. These water-soluble polymers may be synthesized by free radical initiation of the vinyl monomers listed above. Such a free radical initiation may be accomplished using any free radical initiator known in the art, such as organic peroxides, Vazo compounds, and/or Redox free radical initiators. These catalysts are well known in the art. In addition, these polymers may be synthesized as solution polymers in aqueous media, or they may be synthesized in non-aqueous media when such is necessary to obtain polymers, for example, when copolymerizing with maleic anhydride. Finally, these polymers may be synthesized using water-in-oil emulsion polymerization techniques as taught in U.S. Pat. No. Re. 28,474, U.S. Pat. No. Re. 28,576, and U.S. Pat. No. 3,284,393, all of which are incorporated herein by reference.

The polymers of the instant invention are formed using the monomers described above, are water-soluble, and may be combined with cellulosic fibers to form an improved paper sheet with strength characteristics that to date has been unattainable.

The water-soluble polymers of this invention contain at least 2 mole percent of a monomer represented by the chemical structure:

$$+CH_2-\overset{R}{\underset{}{C}}+$$
$$\overset{|}{C=O}$$
$$\overset{|}{A+B+_{\overline{n}}D}$$

wherein
R is —H, —$CH_3$, or —$C_2H_5$; and
A is O, or N($R_1$); and
B is $CH_2$, $CH_2CH_2O$, $+CH_2+_{\overline{n}}N(R_1)$ ($CH_2+_{\overline{m}}$, $$+CH_2+_{\overline{n}}\overset{R_1}{\underset{R_2}{N^{(+)}}}+CH_2+_{\overline{m}} \quad (Z)^-;$$

and
D is $$+CH_2+_{\overline{m}}CH\overset{O}{\underset{O}{\diagdown}}R_3 \quad \text{or} \quad +CH_2+_{\overline{m}}\overset{OR_4}{\underset{OR_5}{CH}};$$

and
wherein $R_1$ is —H, —$CH_3$, —$C_2H_5$, $(CH_2CH_2O)_nH$, or $(B)_qD$, and wherein q is from 1–6, except when B contains nitrogen in which case q is always one; and wherein $R_2$ is —H, —$CH_3$, —$C_2H_5$, or $(CH_2CH_2O)_nH$; and wherein $R_3$ is $$+C+_{\overline{n}}\overset{R_4}{\underset{R_5}{\diagdown}};$$

and wherein $R_4$ and $R_5$ may be the same or different and are, for each individual occurance, —H, —$CH_3$, or —$C_2H_5$; and wherein Z is from the group Cl, Br, I, $NO_3$, $SO_4$ and the like; and wherein m ranges from 0–6; and wherein n is from 1–6.

Where we use $R_3$ as

we mean to include cyclic acetals such as:

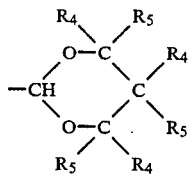

Wherein each $R_4$ and $R_5$ are individually chosen from —H, —CH$_3$ or —C$_2$H$_5$.

The preferred water-soluble polymer for use in this invention contains at least 10 mole percent of a repeating monomer unit represented by the structure:

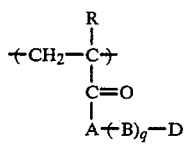

wherein
R is H or —CH$_3$
A is —O— or —N(R$_1$)—
B is —CH$_2$—,

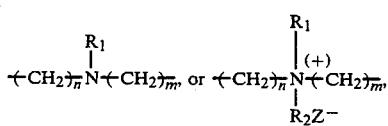

and
wherein
D is

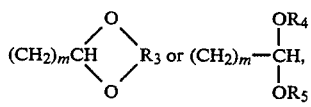

and wherein q, m, n, $R_1$, $R_2$, $R_3$, $R_4$, $R_5$ and Z have the same meaning as above.

The water-soluble polymers of our invention may be homopolymers or they may be copolymers, but if they are copolymers, they must contain at least 2 mole percent of the monomers described above, preferably 10 mole percent of the monomers described above, and most preferably at least 50 mole percent of the monomers described above.

When the water-soluble polymers of this invention contain other monomers to form copolymers, terpolymers and the like, the polymers may additionally contain vinyl monomers chosen from the group consisting of acrylamide, methacrylamide, N-methylacrylamide, and N,N-dimethylacrylamide, acrylonitrile, acrylic acid, methacrylic acid, vinyl sulfonate, AMPS[1], vinyl acetate, DADMAC[2], MAPTAC[3], DMAPMA[4], DMAEM[5] and its quaternary salts, DMAEA[6] and its quaternary salts, ethyl acrylate, methyl acrylate, N-vinyl pyrollidone, or any mixtures thereof.

[1]AMPS=Acrylamidopropane sulfonic acid
[2]DADMAC=Diallyl dimethyl ammonium chloride
[3]MAPTAC=Methacrylamidopropyl trimethyl ammonium chloride
[4]DMAPMA=Dimethylaminopropyl methacrylamide
[5]DMAEM=Dimethylamino ethyl methacrylate
[6]DMAEA=Dimethylamino ethyl acrylate The water-soluble polymers may contain active hydrogen functionality since this functionality can be reactive with the aldehyde and hemiacetals which are present in the monomers used to form the water-soluble polymers of this invention and under appropriate conditions can cause crosslinking or thermosetting properties. However, these crosslinking rections can be controlled by the original formation of a water-soluble polymer in the acetal form which, when applied to paper, is hydrolyzed in situ forming the hemiacetal or aquated aldehyde which then subsequently combines with cellulosic fibers leading to the improved paper strength properties found in this invention.

The preferred water-soluble polymers of this invention are those polymers which are copolymers with cationically charged monomers. These cationically charged monomers may be chosen from the group consisting of MAPTAC, DADMAC, DMAEM and its quaternary salts, DMAEA and its quaternary salts, and/or monomers represented by the structure:

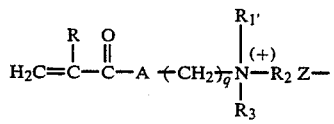

wherein R is —H, —CH$_3$, or C$_2$H$_5$, and A=—O—, or

and wherein $R_1$, $R_2$, and $R_3$ may be the same or different and are —H, —CH$_3$, —C$_2$H$_5$, or (Ch$_2$CH$_2$O)$_q$H; q is between 1–6; and Z is Cl, Br, and I, and mixtures thereof.

Although we have listed several cationic monomers which form copolymers with the monomers of this invention, other cationic monomers which are capable of free radical vinyl polymerization may also be used and are meant to be included in this invention.

The water-soluble polymers of this invention may also include copolymers with anionic monomers. Such anionic monomers may be chosen from the group consisting of acrylic acid, methacrylic acid, maleic anhydride, vinyl sulfonate, AMPS, sulfonated styrene, and monomers represented by the structure:

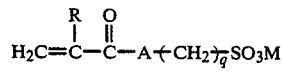

wherein
R=H, CH$_3$, or C$_2$H$_5$
A=—O— or —N(R)—
M=H, Na, Li, K, Mg, Ca, and the like, and
q is between 1–6,
and mixtures thereof.

In addition, the polymers of this invention may include copolymers with neutral water-soluble monomers or copolymers of a neutral character which, when polymerized with the monomers of this invention, form water-soluble polymers. These neutral monomers may be chosen from the group consisting of acrylamide, methacrylamide, N-substituted acrylamides or methacrylamides, ethoxylated acrylamides, N-vinyl pyrollidone, ethyl acrylate, methyl acrylate, vinyl acetate, and mixtures thereof.

Finally, the copolymers of this invention may contain more than 2 monomers, either chosen from preferred structures of the monomers of this invention or chosen from any of the listed monomers above. For example, terpolymers of acrylamide, the preferred monomers above, and, DADMAC may be easily synthesized and used to improve strength characteristics in paper sheet when combined with the cellulosic fibers making up the paper sheet.

The water-soluble polymers of this invention must have a molecular weight of at least 1,000, and preferably they have a molecular weight of at least 5,000. When certain monomers are used in combination with the monomers of this invention, the water-soluble polymers of this invention may have molecular weights exceeding 1,000,000.

The polymers of this invention may also be made by chemical adduction of reactive compounds onto the backbone of existing polymeric species. For example, vinyl polymers having appropriate reactive substituents and the chemicals described above may be reacted to accomplish a chemical adduction to yield homopolymers or the co- and/or ter-polymers of this invention.

For example a polyacrylonitrile may be dispersed or dissolved in an appropriate reaction media: then reacted with anhydrous ferric chloride and the reactant R'Z, where Z=Cl, Br, I and the like, and where R'=

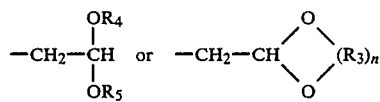

and where $R_3=$

$R_4$ and $R_5$ are the same or different and may, at each individual occurrence, be H, $-CH_3$, $-C_2H_5$ and the like, and n=1–6.

This adducted polymer is then reacted with water to yield a polymer of this invention. Similarly cationically modified acrylamide or copolymers of acrylamide containing amino substitution may be quaternized with the reactant R'Z above to yield the polymers of this invention, i.e.:

A polymer represented by:

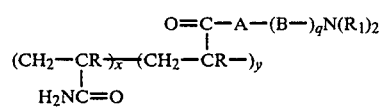

may be reacted with the reactant R'Z above to achieve the copolymer of the invention. In this example, if x is zero, and the chemical adduction is complete, a homopolymer would be expected, if x and y are both not zero, and the adduction reaction with R'Z is complete, a copolymer would be expected, and if x is zero, and the adduction is incomplete a copolymer is expected, or if x and y are both not zero and the adduction reaction is not complete, a terpolymer is expected.

Finally, polymers of this invention may be manufactured by reacting dispersed or dissolved polymer, in an appropriate solvent, in the following reaction sequence:

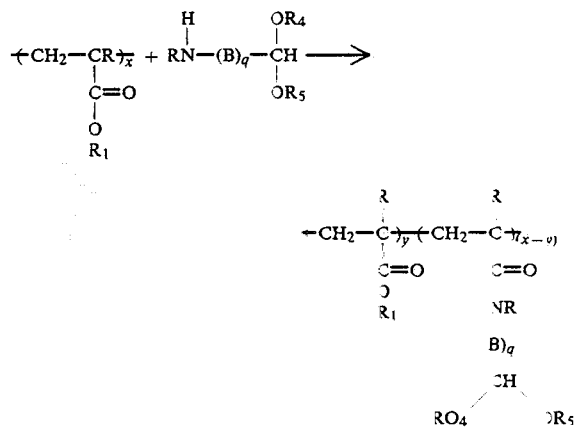

wherein R may be H, $CH_3$, $C_2H_5$ and the like; and $R_1$ may be same or different as R, and y and x are normally greater than 10, but y may be zero, and B, q, $R_4$ and $R_5$ have their previous meaning.

PAPER COMPOSITIONS

The paper compositions of this invention comprise cellulosic fibers combined with a water-soluble polymer which contains at least 2 mole percent of a monomer represented by the chemical structure:

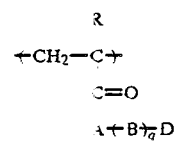

wherein
R is $-H$, $-CH_3$, or $-C_2H_5$; and
A is O, or $N(R_1)$; and
B is $CH_2$, $CH_2CH_2O$, $+CH_2\!\!+_{\!\!n} N(R_1) (CH_2\!\!+_{\!\!m}$,

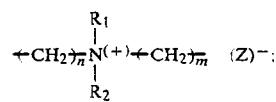

and
D is

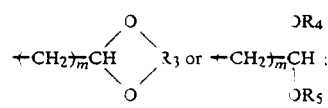

and
wherein $R_1$ is $-H$, $-CH_3$, $-C_2H_5$, $(CH_2CH_2O)_nH$, or $(B)_q D$, and wherein q is from 1–6, except when B contains nitrogen in which case q is always one; and wherein $R_2$ is —H, —$CH_3$, —$C_2H_5$, or $(CH_2CH_2O)_nH$; and wherein $R_3$ is

and wherein $R_4$ and $R_5$ may be the same or different and are, for each individual occurance, —H, —$CH_3$, or —$C_2H_5$; and wherein Z is from the group Cl, Br, I, $NO_3$, $SO_4$ and the like; and wherein m ranges from 0–6; and wherein n is from 1–6.

Again, the cyclic acetals which are assymetrically substituted are included in these definitions.

The word "paper" is herein used to include any cellulose containing mat or web which is prepared by screening a dilute cellulose fiber suspension, which may or may not contain other fibrous matter such as rayon, nylon, glass fiber and the like, in water. Examples of this include:

Non-woven fabrics
roofing felt
molded products (e.g. egg cartons)
ceiling tile

The paper compositions above may contain the cellulosic fibers and the water-soluble polymers described above dispersed one within the other such that no significant concentration gradient of polymer exists within the paper sheet. This is usually accomplished by admixing the water-soluble polymers of this invention with the cellulosic fibers prior to paper sheet formation. However, this may also be accomplished by adding solutions of the water-soluble polymers described above to a preformed sheet and then drying.

The paper compositions may also contain the water-soluble polymer combined with only the surface cellulosic fibers on the surfaces of the paper sheet. This is most likely accomplished by spraying the solutions of the polymer onto a preformed paper sheet or applying solutions of the polymer to the paper sheet using draw down knives, brushes, low pressure sprays, and such other application techniques. It is preferred that the paper composition comprise cellulosic fibers combined with the water-soluble polymers described above such that no concentration gradient of the polymer exists within the paper.

Test procedures used to define wet strength, dry strength, and the like are found in TAPPI Official Test Method T 494 om-81 and is a TAPPI Official Test Method published in 1981. This method allows tensile breaking properties of paper and paperboard using constant rate of elongation apparatus to be properly measured. The test referred to above is a TAPPI test for dry strength. We have modified this test to test wet strength in the following manner: a paper sheet cut to appropriate dimensions is inserted into the test apparatus. A camelhair brush is used to wet the test strip in its center while the sample is in the jaws of the test equipment. De-ionized water is always used to wet the test strip. After the water has been applied using the camelhair brush for 10 seconds, the test strip is broken in the tester and the wet strength measured thereby. Testing methods for wet web strength are found in Scandanavian Pulp, Paper and Board Testing committee SCAN-C 35:81, and SCAN-M 12:81, and R. S. Seth, et al, TAPPI 65 (3) 135 (1982), which is incorporated herein by reference.

To better describe the preparation of the monomers of this invention, the water-soluble polymers of this invention, and their use in forming paper sheet having improved strength by combining cellulosic fibers with the water-soluble polymers described above, the following examples are presented.

EXAMPLES

Example 1

Preparation of N-(2,2 dimethoxyethyl)acrylamide:

A 3000 ml. round bottom flask was fitted with a mechanical stirrer, a dropping funnel, a thermometer, and a dry ice reflux condenser. To the flask was charged 271.9 grams of aminoacetaldehyde dimethylacetal dissolved in 1295 ml. of ethyl ether. To the dropping funnel was charged 117.0 grams of acryloylchloride dissolved in 430 ml. of ethyl ether.

The round bottom flask was suspended in a dry ice-isopropanol bath. When the contents reached 0° C., the acryloylchloride solution was allowed to slowly drip into the flask. Temperature was maintained at 0° to 3° C. over a 40 minute period during which all the acryloylchloride solution had been added. Voluminous white crystals of aminoacetaldehyde dimethylacetal hydrochloride were present in the product. These crystals were removed via filtration. Methoxyhydroquinone (0.1 gram) was added and the filtrate was concentrated by evaporation of the ethyl ether to yield 189 grams of N-(2,2 dimethoxyethyl)acrylamide (92% yield).

Example 2

Preparation of N-methyl, N-(2,2 dimethoxyethyl)acrylamide:

This monomer was prepared in a manner similar to that of Example 1. Charged to the flask was 300 grams of methylaminoacetaldehyde dimethylacetal dissolved in 1300 ml. of ethyl ether. Charged to the dropping funnel was 114 grams of acryloyl chloride dissolved in 420 ml. of ethyl ether. The acryloyl chloride solution was added during a 35 minute period while maintaining —10° to —5° C. The slurry of amine hydrochloride that formed was very viscous. An additional 350 ml. of ethyl ether was added to minimize this.

Isolation of the product was as described in Example 1. Yield was 161 grams (74%).

Example 3

Preparation of 2,2 diethoxyethyl-methacrylate:

A one liter round bottom flask was equipped with a mechanical stirrer, thermometer, and reflux condenser. Charged initially to the flask were 210.5 grams of triethylamine followed by 179.0 grams of methacrylic acid. A water bath was used to keep the temperature near ambient during this step.

When all the methacrylic acid had been charged, 410.0 grams of bromoacetaldehyde diethylacetal was added. This mixture was then heated to reflux (approximately 123° C.) for a period of 38 hours. During this period the temperature ranged between 123° and 138° C. White crystals of triethylamine hydrobromide formed in the solution and at one point sublimed into the condenser.

The crystals were filtered and washed with 300 ml. of ethyl ether. These filtrates were combined and washed with two 1000 ml. portions of water containing a small amount of sodium sulfate. Additional quantities of ethyl ether (total of 500 ml.) were added to effect a reasonably good separation of the phases in a separatory funnel.

The ether solution of the product was dried with 150 grams of anhydrous potassium carbonate. After removal of the ethyl ether via distillation, the product was fractionally distilled to yield:

1. 15.2 grams (b.p.=23°-62° C./16 mm.)
2. 56.9 grams (b.p.=71°-90° C./16 mm.)
3. 124.0 grams (b.p.=94°-108° C./16 mm.)

Analysis indicated that fraction #1 was predominantly ethyl methacrylate. Fraction #2 was predominantly bromoacetaldehyde diethylacetal. Fraction #3 was the desired product, 2,2 diethoxy-ethyl-methacrylate (29% yield).

Examples 4 and #5

Preparation of:
(a) N-(2-hydroxy, 2-methoxyethyl)acrylamide;
(b) N-(2,2 dihydroxyethyl)acrylamide;
(c) N-methyl, N-(2-hydroxy, 2-methoxyethyl)acrylamide;
(d) N-methyl, N-(2,2 dihydroxyethyl)acrylamide.

These monomers were prepared by the acid hydrolysis of the monomers described in Examples #1 and #2. The experiments were carried out in NMR tubes and the spectra proved the structures to be the compounds sought to be synthesized.

Example 6

Preparation of the copolymer of N-(2,2 dimethoxyethyl)acrylamide with methacrylamidopropyl trimethyl ammonium chloride:

Combined in a 50 ml. beaker on a magnetic stir plate was:
15.1 grams of the monomer described in Example #1;
2.2 grams of a 50% aqueous solution of methacrylamidopropyl trimethyl ammonium chloride;
14.54 grams water;
0.05 grams ammonium persulfate.

To this solution was added 0.11 grams of sodium meta bisulfite dissolved in 4.0 grams of water. Upon addition of the sodium metabisulfite solution the mixture exothermed from 26° C. to 77° C. during a four minute period. The viscous polymer solution that resulted was determined to be of molecular weight approximately equal to 37,000.

Example 7

Preparation of the terpolymer of N-(2,2 dimethoxyethyl)acrylamide; acrylamide; and dimethyl-diallyl-ammonium chloride:

Charged to a Dewar flask equipped with a thermometer and mechanical stirrer were the following:
10.2 grams of a 49% aqueous dimethyl-diallyl-ammonium chloride solution
52.6 grams of a 42.8% aqueous solution of acrylamide
102.2 grams of a 50% aqueous solution of N-(2,2 dimethoxyethyl)acrylamide
75.9 grams of water The mixture was adjusted to pH=8.5 with sodium hydroxide. There was then added in rapid succession:
a solution of 0.167 grams of ammonium persulfate in 5.0 grams of water.
a solution of 0.333 grams of sodium metabisulfite dissolved in 5.0 grams of water.

Upon addition of the last ingredient the reaction mixture exothermed from 21.5° C. to 71.8° C. during a six minute period.

The viscous solution that resulted was determined to contain polymer of molecular weight approximately equal to 55,000.

TABLE I

| Example Number | Polymer Composition | Monomer Ratio (w/w) | Polymer Concentration in water | Polymer Molecular Weight | % by weight of a 2/1, (w/w), sodium-metabisulfite/ammonium persulfate initiator (BOM) |
|---|---|---|---|---|---|
| #8 | N—(2,2 dimethoxyethyl) acrylamide/dimethyl-diallyl-ammonium chloride | 95.3/4.7 | 42.3% | 35,000 | 0.47% |
| #9 | N—(2,2 dimethoxyethyl) acrylamide/acrylamide/dimethyl-diallyl-ammonium chloride | 64.7/28.9/6.4 | 31.2% | 2,500,000 | Initiator was 0.0963% ammonium persulfate; 0.0032% ferrous ammonium sulfate .6H$_2$O); 0.0096% sodium bisulfite (all BOM). |
| #10 | N—(2,2 dimethoxyethyl) acrylamide | 100 | 44.8% | 41,000 | 0.56% |
| #11 | N—methyl, N—(2,2 dimethoxyethyl) acrylamide/acrylamide/dimethyl-diallyl-ammonium chloride | 66.6/27.3/6.1 | 32.8% | 350,000 | 0.76% |
| #12 | N—methyl,N—(2,2 dimethoxyethyl) acrylamide/dimethyl-diallyl-ammonium chloride | 95.6/4.4 | 44.7% | 96,000 | 0.55% |

Example 13

Polymerization of 2,2 diethoxyethyl methacrylate:

The monomer of Example #3 was polymerized as follows: A 250 ml., three neck flask was equipped with a stirrer, thermometer, nitrogen inlet, and nitrogen outlet. Charged to the flask were:
92.75 grams of water
1.25 grams disodium hydrogen phosphate
6.00 grams Triton X-200 (Rohm & Haas)
50.00 grams 2,2 diethoxyethyl methacrylate This mixture was adjusted to pH=7.5 with hydrochloric acid. The following were then added:
1.00 gram of a 0.15% aqueous solution of ferrous sulfate (0.7H$_2$O)
0.25 gram of ammonium persulfate
2 drops of tert-butyl hydroperoxide (70%)
0.25 gram of sodium meta-bisulfite During this period of time the reaction mixture exothermed from 21° C. to 46° C. The final product was a white latex polymer which contained approximately 11 grams of coagulum which was separated and discarded. Evaporation of the water in a portion of the finished polymer left a clear flexible residue equal to 33% of the initial weight.

Example #14

Hydrolysis of the polymer of Example #8:

The following mixture was prepared:
25 grams of a 42.3% aqueous solution of the copolymer of N-(2,2 dimethoxyethyl)acrylamide with dimethyl-diallyl-ammonium chloride (see Example #8)
50 grams of 0.5 normal hydrochloric acid
25 grams of water This mixture was placed in a bottle and immersed in a 30.0° C. water bath. The hydrolysis of the acetal groups in the polymer to yield both hemiacetal and hydrated aldehyde groups was followed with time by withdrawing aliquotes of the reaction mixture and titrating them. The titration procedure was a modification of that of Bryant (*J. Am. Chem. Soc.*, Vol. 57, p.57ff, 1935). The modifications consisted of:

(a) Use of anhydrous solvents for reagent preparation (thus allowing larger introduction of water with the samples).

(b) Incorporating a "pre-titration" of the acidity of the sample due to the use of hydrochloric acid to promote hydrolysis. This is done prior to the introduction of the pyridine or hydroxylamine hydrochloride reagents.

(c) Incorporating a reaction period of 20 minutes at 70° C. for reaction of the hydroxylamine hydrochloride with the sample.

(d) Use of a filtration step prior to the final titration with necessary to remove generated solids. From another experiment (see NMR/titration results), it has been determined that a "conversion" thus determined is the sum of hemiacetal and hydrated aldehyde groups.

Using the above procedures, the following data was generated during the above hydrolysis experiment.

TABLE II

| Elapsed Time | Meg. of Acidity per gram of sample (pre-titration) | Meg./gram (final titration) | Acetal Conversion |
|---|---|---|---|
| 0 hour | 0.244 | 0.000 | 0% |
| 1 hour | 0.243 | 0.166 | 26% |
| 2½ hours | 0.242 | 0.332 | 52% |
| 3⅞ hours | 0.242 | 0.434 | 68% |
| 22 hours | 0.242 | 0.556 | 88% |

The 22 hour sample showed some signs of gellation. This gel was, however, reversible through further dilution with water.

Example #15

Hydrolysis of the polymer of Example #7:

An experiment similar to that cited in Example #14 was carried out using the terpolymer of Example #7.

Hydrolysis mixture:
25.0 grams of the polymer solution of Example #7;
50.0 grams of 0.5 normal hydrochloric acid;
25.0 grams of water.

TABLE III

| Elapsed Time | Meg./gram Acidity (pretitration) | Meg./gram (Final) | % Acetal Conversion |
|---|---|---|---|
| 0 hour | 0.242 | 0.000 | 0% |

TABLE III-continued

| Elapsed Time | Meg./gram Acidity (pretitration) | Meg./gram (Final) | % Acetal Conversion |
|---|---|---|---|
| 1 hour | 0.244 | 0.080 | 25% |
| 2½ hours | 0.245 | 0.151 | 48% |
| 3⅞ hours | 0.243 | 0.186 | 59% |
| 21 hours | 0.239 | 0.257 | 81% |

Examples #16 to #19

These hydrolysis experiments were carried out in a fashion similar to Examples #14 and #15:

TABLE IV

| Example | Starting Polymer | Conversion Range |
|---|---|---|
| #16 | Example #9 | 0–30% |
| #17 | Example #11 | 0–75% |
| #18 | Example #12 | 0–77% |
| #19 | Example #10 | 0–approx. 80% |

EXAMPLE #20

Cationization of the hydrolyzed homopolymer of N-(2,2 dimethoxyethyl)acrylamide and preparation of a paper composition:

The following mixture was prepared:
10.64 grams of a hydrolyzed 10% solution of poly-N(2,2 dimethoxyethyl)acrylamide (see Example #19);
10.00 grams of a 10% solution of sodium acetate (0.3H$_2$O);
169.36 grams of water;
10.00 grams of an aqueous 0.564% solution of Girard's reagent T.

The pH of this solution was adjusted to 6.0 with sodium hydroxide. A dilute paper fiber slurry was treated with this solution within 1 hour of preparation of the solution. Handsheets prepared from this slurry had much improved wet and dry strength properties as compared to untreated handsheets, indicating a high retention (and successful cationization) of the polymer product. The handsheets were prepared in a semi-automatic British sheet mold from a 50/50 mixture of bleached hardwood kraft/bleached softwood kraft paper fiber. Sheet forming pH was 6.0. The results are shown in Table V.

TABLE V

| Sample | Treatment Level* | Dry Tensile (lb./inch) | Wet Tensile (lb./inch) |
|---|---|---|---|
| Blank | 0% | 37.4 | 1.875 |
| Cationized Polymer | 0.25% | 47.4 | 11.650 |
| Cationized Polymer | 0.50% | 52.1 | 17.700 |
| Cationized Polymer | 0.75% | 56.8 | 20.040 |
| Parez 631NC** | 0.75% | 50.9 | 15.730 |

*Treatment level is % based on fiber of the poly N—(2,2 dimethoxyethyl) acrylamide hydrolysis product. For Parez 631NC, it is active solids as defined by its manufacturer.

**Parez 631NC is a commercial wet strength product manufactured by American Cyanamid. Believed to be a copolymer of 95 parts by weight acrylamide with 5 parts of dimethyl-diallyl-ammonium chloride. This copolymer is then reacted with up to 30 parts (by weight) of glyoxal.

Example #21

Preparation of a paper composition containing hydrolyzed and cationized poly-N-(2,2 dimethoxyethyl)acrylamide:

The hydrolyzed and cationized polymer solution described in Example #20 was used to saturate samples of Whatman No. 1 filter paper. The saturated paper samples were dried in a 215° F. oven for 10 minutes. Through proper dilution of the saturating solutions, a range of treatment levels are obtained. Solution pH's were maintained at 6.0. The results are shown in Table VI.

TABLE VI

| Sample | Treatment Level* | Dry Tensile (lb./inch) | Wet Tensile (lb./inch) |
|---|---|---|---|
| Blank | 0% | 12.8 | 0.700 |
| Cationized Polymer | 0.25% | 15.1 | 3.910 |
| Cationized Polymer | 0.50% | 16.9 | 5.083 |
| Cationized Polymer | 0.75% | 18.1 | 7.600 |
| Parez 631NC** | 0.75% | 16.8 | 4.353 |

*See Example #20.
**See Example #20.

Example #22

Preparation of paper compositions containing hydrolyzed polymers of differing conversions:

The following materials were charged to a bottle which was then placed in a 30.0° C. water bath during the hydrolysis period:
   25 grams of the polymer solution of Example #7;
   25 grams of water;
   50 grams of 0.5 normal hydrochloric acid.

At the times indicated, samples were withdrawn and titrated to determine extent of conversion. Separate samples were withdrawn and diluted as follows:
   6.88 grams of sample from the above mixture;
   5.00 grams of a 10% $NaC_2H_3O_2.3H_2O$ solution (buffer);
   88.12 grams of water.

These solutions were adjusted to pH=6.0 with sodium hydroxide. Samples of Whatman No. 1 filter paper were immediately saturated and dryed as described in Example #21. This procedure resulted in 0.75% by weight of the polymer being applied to the paper. The results of this testing are set forth in Table VII.

TABLE VII

| Elapsed Time | % Acetal Conversion | Dry Tensile (lb./inch) | Wet Tensile (lb./inch) |
|---|---|---|---|
| 0 minutes | 0% | 4.09 | 0.24 |
| 100 minutes | 33% | 5.33 | 1.19 |
| 210 minutes | 71% | 6.12 | 1.60 |
| 405 minutes | 73% | 6.10 | 1.59 |
| 1350 minutes | 87% | 6.28 | 1.89 |
| blank | — | 4.70 | 0.28 |

Example #23

Performance of papers prepared on a semi-automatic British sheet mold:

TABLE VIII

| Sample | Wet Web Strength Dose 1% | Wet Web Strength Dose 5% | Rewetted Strength Dose 1% | Rewetted Strength Dose 5% | Dry Strength Dose 1% | Dry Strength Dose 5% |
|---|---|---|---|---|---|---|
| Blank | 232 | 209 | 259 | 297 | 4291 | 4054 |
| Sample A* | 414 | 626 | 2431 | 3605 | 4490 | 4491 |
| Sample B* | 356 | 288 | 2685 | 2700 | 4495 | 4457 |
| Sample C* | 449 | 358 | 3288 | 2918 | 4423 | 4504 |
| Sample D* | 503 | 807 | 2572 | 3607 | 4521 | 4537 |

*Sample A = The polymer of Example #16
*Sample B = The polymer of Example #14
*Sample C = The polymer of Example #15
*Sample D = a glyoxalated acrylamide/DADMAC copolymer.

Note:
1. All results are grams/inch peak load.
2. All product dosages are expressed as equivalent to a 90/10 (w/w), acrylamide/DADMAC backbone (% based on dry fiber).
3. Sheet solids for wet web results is approximately 30–35%.
4. Stock is 92% repulped stock (40% stone groundwood, 40% bleached kraft, 20% TMP) and 8% bleached kraft. Sheets were formed in deionized water at natural pH (approximately 5.7).

Example 24

A solution was prepared from the following in a two liter round bottom flask:
   477.5 gram 2-methyl 2,4 pentanediol
   230.6 gram acrolein (97%)
   528.3 gram methylene chloride The flask was then fitted with a mechanical stirrer, gas inlet tube, therometer, and dry ice condensor. The flask was immersed in a dry ice/isopropanol bath and cooled to −10° C. At this time anhydrous hydrogen chloride gas was bubbled into the solution until no more gas was absorbed. Temperature was maintained at approximately −10° C. throughout this process.

After the gas absorption was complete the material was warmed to ambient temperature and the bottom aqueous layer separated and discarded. Following this, the organic layer was washed with water, neutralized with a sodium bicarbonate solution and dried over magnesium sulfate. The filtered product was relieved of methylene chloride by distillation. The product was 793.5 grams of 2-(2-chloroethyl)-4,4,6-trimethyl-1,3 dioxane:

$$Cl-CH_2-CH_2-CH \begin{array}{c} O-C(CH_3)-CH_3 \\ \diagdown \\ CH_2 \\ \diagup \\ O-CH-CH_3 \end{array}$$

The following solution was prepared in a bench top autoclave:
   84.7 gram product I. (above)
   84.7 gram methanol
   74.8 gram dimethylaminopropyl methacrylamide The autoclave was sealed and heated to 100°–110° C. for a period of approximately six hours. NMR spectral examination of the final method solution indicated an approximate 80% conversion to:

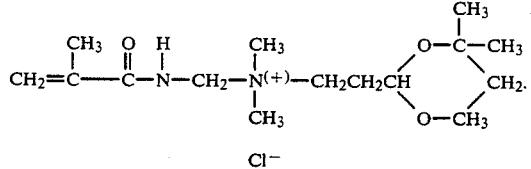

The following is a list of potential reactants which would give monomers described in Table IX if reacted together according to the previous teachings above.

1. Reactant A (a vinyl containing moiety):

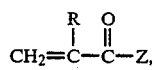

where Z=Cl, Br, I

2. Reactant B (an acetal containing moiety): H—A—(B)q—D

3. Reactant C (a vinyl containing moiety):

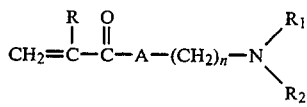

4. Reactant D (an acetal containing moiety): X—(CH$_2$)$_m$—D

If the monomers shown in Table IX where combined with themselves or with any of the above mentioned comonomers, the water-soluble polymers of this invention would be expected to form. If these water-soluble polymers were then reacted with a cellulosic substrate a paper composition of this invention would be expected to form.

TABLE IX

| Reactant Combination | R | A | B | q | D | n | $R_1$ | $R_2$ | Z | m | Monomer Produced |
|---|---|---|---|---|---|---|---|---|---|---|---|
| A + B | $-C_2H_5$ | $\underset{\mid}{-N-R_1}$ | $-CH_2-$ | 1 | $-CH(OCH_3)_2$ | — | $-H$ | — | — | — | $CH_2=C-C-N-CH_2CH(OCH_3)_2$ with $\overset{O}{\|}$, $\overset{H}{\|}$, $C_2H_5$ |
| A + B | $-H$ | $\underset{\mid}{-N-R_1}$ | $-CH_2-$ | 2 | $-CH(OCH_3)_2$ | — | $-H$ | — | — | — | $CH_2=CH-C-N-CH_2CH_2CH(OCH_3)_2$ with $\overset{O}{\|}$, $\overset{H}{\|}$ |
| A + B | $-H$ | $\underset{\mid}{-N-R_1}$ | $-CH_2-$ | 6 | $\underset{O-CH_2}{\overset{O-CH_2}{\diagdown CH \diagup}}$ | — | $-(CH_2CH_2O)_mH$ | — | — | 2 | $CH_2=CH-C-N-(CH_2)_6-N[\,H(OCH_2CH_2)_2\,]$ with $\overset{O}{\|}$, and bicyclic acetal group |
| A + B | $-H$ | $\underset{\mid}{-N-R_1}$ | $-CH_2-$ | 2 | $-CH_2-CH-(OCH_3)_2$ | — | $-(B)_q-D$ | — | — | — | $CH_2=CH-C-N[CH_2-CH_2-CH_2CH(OCH_3)_2]_2$ with $\overset{O}{\|}$ |
| C + D | $-CH_3$ | $-O-$ | $-(CH_2)_n-\underset{R_2}{\overset{R}{\mid}}\overset{(+)}{N}-(CH_2)_m-$ | 1 | $-CH_2-CH(OCH_3)_2$ | 2 | $CH_3-$ | $CH_3-$ | $-Br$ | 1-6 | $CH_2=C-C-O-CH_2CH_2-\underset{CH_3}{\overset{CH_3}{\mid}}\overset{(+)}{N}-(CH_2)_{1-6}CH_2CH(OCH_3)_2 \; Br^-$ |
| A + B | $-H$ | $-O-$ | $-CH_2CH_2O-$ | 1-6 | $-CH_2CH(OCH_3)_2$ | — | — | — | — | — | $CH_2=CH-C-O(CH_2CH_2-O-)_{1-6}CH_2-CH(OCH_3)_2$ with $\overset{O}{\|}$ |
| A + B | $-H$ | $\underset{\mid}{-N-R_1}$ | $-CH_2-$ | 2 | $(CH_2)_{0-6}CH(OCH_3)_2$ | — | $-C_2H_5$ | — | — | 0 | $CH_2=CH-C-O-N-(CH_2)_2(CH_2)_{0-6}CH(OCH_3)_2$ with $C_2H_5$ |

As can be seen from the data presented above, the water-soluble polymers of this instant invention are readily formed from the monomers of this invention. These monomers are capable of polymerization to give stable products of linear polymers of relatively high molecular weight. It is important that the acetal functionality be hydrolyzed to form the hemiacetal or free aldehyde functionality to obtain the strength properties above. To do so, the method of Bryant, which is incorporated herein by reference, as published in the *Journal of the American Chemical Society* in 1935, was adapted to follow the acetal hydrolysis of the products of this invention.

In addition, Nuclear Magnetic Resonance experiments were used to follow the acetal hydrolysis. These results confirm the anticipated structure of the polyacetal materials and have not detected any amide hydrolysis which may be simultaneously competitive with the acetal hydrolysis. In addition, the Nuclear Magnetic Resonance studies referred to above suggest that both hemiacetal and hydrated aldehydes are produced when the acetal structures are hydrolyzed. Our work seems to indicate that both hemiacetal as well as hydrated aldehyde structures are reactive when combined with cellulosic fibers and do form paper compositions having improved paper strength properties. However, it would seem apparent from the results above that the degree of acetal hydrolysis relates to the performance of the hydrolyzed polymers as a paper strengthening agent. Therefore, high conversion of acetal to hemiacetal and hydrated aldehyde is very desirable.

The data presented above also indicates that a dose performance improvement is observed when the polymers of the instant invention are compared with the polymers commercially available under the teachings of U.S. Pat. No. 3,556,932, previously incorporated herein by reference.

Having described our inventions, we claim:

1. A paper composition which comprises cellulosic fibers combined with an amount of a water-soluble polymer sufficient to increase the strength of the paper said water soluble polymer contains at least two mole percent of a monomer represented by the chemical structure:

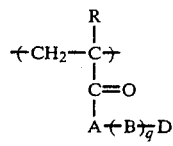

wherein
R is —H, —CH$_3$, or —C$_2$H$_5$; and
A is O, or N(R$_1$); and
B is CH$_2$, CH$_2$CH$_2$O, $-(CH_2)_{\overline{n}}N(R_1)(CH_2)_{\overline{m}}$,

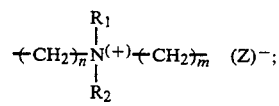

and
D is

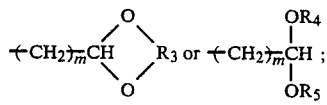

and
wherein R$_1$ is —H, —CH$_3$, —C$_2$H$_5$, (CH$_2$CH$_2$O)$_n$H, or (B)$_q$D, and wherein q is from 1–6, except when B contains nitrogen in which case q is always one; and wherein R$_2$ is —H, —CH$_3$, —C$_2$H$_5$, or (CH$_2$CH$_2$O)$_n$H; and wherein R$_3$ is

and wherein R$_4$ and R$_5$ may be the same or different and are, for each individual occurance, —H, —CH$_3$, or —C$_2$H$_5$; and wherein Z is from the group Cl, Br, I, NO$_3$, SO$_4$ and the like; and wherein m ranges from 0–6; and wherein n is from 1–6.

2. The paper composition of claim 1 wherein the cellulosic fibers and water-soluble polymer are dispersed one within the other such that no concentration gradient of polymer exists within the paper.

3. The paper composition of claim 1 wherein the water-soluble polymer is combined with the cellulosic fibers on the surfaces of the paper.

* * * * *